(12) United States Patent
Boehling et al.

(10) Patent No.: US 8,212,069 B2
(45) Date of Patent: Jul. 3, 2012

(54) PROCESS FOR PREPARING ISOCYANATES

(76) Inventors: Ralf Boehling, Lorsch (DE); Sven Kueber, Kallstadt (DE); Stefan Maixner, Schwetzingen (DE); Eckhard Stroefer, Mannheim (DE); Jochem Henkelmann, Mannheim (DE); Georg Krug, Moerlenbach (DE); Werner Bolz, Ludwigshafen (DE)

(*) Notice: Subject to any disclaimer, the term of this patent is extended or adjusted under 35 U.S.C. 154(b) by 369 days.

(21) Appl. No.: 12/446,460

(22) PCT Filed: Oct. 18, 2007

(86) PCT No.: PCT/EP2007/061153
§ 371 (c)(1),
(2), (4) Date: May 26, 2009

(87) PCT Pub. No.: WO2008/049783
PCT Pub. Date: May 2, 2008

(65) Prior Publication Data
US 2010/0317889 A1 Dec. 16, 2010

(30) Foreign Application Priority Data
Oct. 26, 2006 (EP) .................................... 06123015

(51) Int. Cl.
C07C 263/00 (2006.01)
(52) U.S. Cl. ...................................................... 560/347
(58) Field of Classification Search .................. None
See application file for complete search history.

(56) References Cited

U.S. PATENT DOCUMENTS

| | | | |
|---|---|---|---|
| 6,225,497 B1 * | 5/2001 | Becker et al. ............. | 560/347 |
| 7,235,697 B2 | 6/2007 | Muller et al. | |
| 2003/0166965 A1 | 9/2003 | Wolfert et al. | |
| 2005/0222453 A1 * | 10/2005 | Woelfert et al. ........... | 560/347 |
| 2006/0173218 A1 | 8/2006 | Muller et al. | |
| 2007/0299282 A1 | 12/2007 | Rohde et al. | |
| 2008/0146848 A1 | 6/2008 | Vanoppen et al. | |
| 2008/0159948 A1 | 7/2008 | Sesing et al. | |
| 2008/0171894 A1 | 7/2008 | Muller et al. | |
| 2008/0194845 A1 | 8/2008 | Lang et al. | |
| 2008/0200721 A1 | 8/2008 | Muller et al. | |
| 2008/0200722 A1 | 8/2008 | Wolfert et al. | |
| 2008/0207954 A1 | 8/2008 | Stroefer et al. | |
| 2008/0207955 A1 | 8/2008 | Stroefer et al. | |
| 2008/0216390 A1 | 9/2008 | Tebben et al. | |
| 2008/0221368 A1 | 9/2008 | Stroefer et al. | |
| 2008/0249332 A1 | 10/2008 | Klotzer et al. | |
| 2008/0255376 A1 | 10/2008 | Siegert et al. | |
| 2008/0262263 A1 | 10/2008 | Wolfert et al. | |
| 2008/0281109 A1 | 11/2008 | Lang et al. | |
| 2008/0306316 A1 | 12/2008 | Becker et al. | |
| 2008/0308765 A1 | 12/2008 | Staffel et al. | |
| 2008/0319230 A1 | 12/2008 | Sigl et al. | |
| 2009/0112017 A1 | 4/2009 | Sesing et al. | |
| 2009/0112018 A1 | 4/2009 | Sesing et al. | |
| 2009/0131657 A1 | 5/2009 | Staffel et al. | |

FOREIGN PATENT DOCUMENTS

| | | |
|---|---|---|
| DE | 1 768 439 | 11/1971 |
| DE | 198 04 915 | 8/1999 |
| DE | 100 26 142 | 12/2001 |
| EP | 0 570 799 | 11/1993 |
| EP | 0 593 334 | 4/1994 |
| EP | 0 699 657 | 3/1996 |
| EP | 0 792 263 | 8/1999 |
| EP | 1 073 628 | 10/2003 |
| WO | 01 91898 | 12/2001 |
| WO | 03 099770 | 12/2003 |

OTHER PUBLICATIONS

Ehrfeld, W. et al., "State of The Art of Microreaction Technology", Microreactors: New Technology for Modern Chemistry, pp. 1-14 (2000) XP 002465177.
U.S. Appl. No. 11/721,588, filed Jun. 13, 2007, Osswald, et al.
U.S. Appl. No. 11/916,600, filed Dec. 5, 2007, Fiene, et al.
U.S. Appl. No. 11/993,777, filed Dec. 21, 2007, Van Laar, et al.
U.S. Appl. No. 12/063,171, filed Feb. 7, 2008, Lang, et al.
U.S. Appl. No. 12/065,964, filed Mar. 6, 2008, Woelfert, et al.
U.S. Appl. No. 12/160,433, filed Jul. 10, 2008, Kloetzer, et al.
U.S. Appl. No. 12/161,349, filed Jul. 18, 2008, Hoffer, et al.
U.S. Appl. No. 60/778,371, filed Mar. 3, 2006, Henkelmann.
U.S. Appl. No. 12/281,406, filed Sep. 2, 2008, Henkelmann, et al.
U.S. Appl. No. 12/302,162, filed Nov. 24, 2008, Loeffler, et al.
U.S. Appl. No. 12/304,223, filed Dec. 10, 2008, Siegert, et al.
U.S. Appl. No. 12/307,759, filed Jan. 7, 2009, Knoesche, et al.
U.S. Appl. No. 12/374,351, filed Jan. 19, 2009, Degen, et al.
U.S. Appl. No. 12/375,759, filed Jan. 30, 2009, Henkelmann, et al.
U.S. Appl. No. 12/375,598, filed Jan. 29, 2009, Henkelmann, et al.
U.S. Appl. No. 12/373,088, filed Jan. 9, 2009, Fiene, et al.
U.S. Appl. No. 12/438,086, filed Feb. 19, 2009, Kloetzer, et al.
U.S. Appl. No. 12/598,934, filed Nov. 5, 2009, Tishkov, et al.
U.S. Appl. No. 12/678,771, filed Mar. 18, 2010, Knoesche, et al.
U.S. Appl. No. 13/062,732, filed Jun. 6, 2011, Machhammer, et al.

* cited by examiner

Primary Examiner — Susanna Moore
Assistant Examiner — Jennifer C Sawyer

(57) ABSTRACT

Process for preparing isocyanates by phosgenation of amines, wherein phosgene and amine are brought into contact in at least 2 mixing chambers connected in parallel.

23 Claims, No Drawings

PROCESS FOR PREPARING ISOCYANATES

The invention relates to a preferably continuous process for preparing isocyanates, preferably diisocyanates and/or polyisocyanates, by phosgenation of amines, preferably diamines and/or polyamines, preferably in the liquid phase, wherein phosgene and amine are brought into contact in at least 2, preferably at least 10, particularly preferably at least 100, very particularly preferably from 100 to 100 000, in particular from 100 to 20 000, mixing chambers connected in parallel.

The synthesis of isocyanates, which are important basic products for the production of polyurethanes, is carried out industrially by phosgenation of the corresponding amine. The yields here are above 90%, based on the amine used. This reaction is generally known and has been described many times.

Phosgenation in the liquid phase, which comes into question for, in particular, the preparation of MDI, is described in DE-A 17 68 439, DE-A 198 04 915 and EP-A 1 073 628. Approaches for solving the solids problems which occur in liquid-phase phosgenation due to formation of amine hydrochlorides, ureas, carbamyl chlorides are described in EP-A 792 263, WO 01/91898 and WO 03/99770.

Gas-phase phosgenation as an alternative to phosgenation in the liquid phase has been described, e.g. for the preparation of HDI And TDI, in EP-A 570799, EP-A 699657 and EP-A 593334. A problem in the reaction in the gas phase is the high temperatures necessary, which lead to undesirable by-products and can be kept constant only with difficulty especially in the case of exothermic reactions at the considerable throughputs in industrial plants. In addition, gas-phase phosgenation cannot be employed for the preparation of MDI from crude MDA which further comprises higher homologues.

Disadvantages of the known processes, which are all based on optionally multistage single-stream processes, are thus the solids problems which occur as a result of by-products.

It was thus an object of the present invention to develop a process for preparing isocyanates, in particular MDI, in which solid by-products, in particular, can be avoided as much as possible. Although these problems can be solved to a certain extent by increasing the excess of phosgene, a further object is to minimize the phosgene hold-up in the plant, i.e. the amount of phosgene present in the plant. Furthermore, the isocyanate which can be obtained should have a very good property profile.

These objects have been able to be achieved by a process for preparing isocyanates, preferably diisocyanates and/or polyisocyanates, particularly preferably MDI and TDI, by phosgenation of amines, preferably diamines and/or polyamines, particularly preferably MDA and TDA, in which phosgene and amine are brought into contact in at least 2, preferably at least 10, particularly preferably at least 100, very particularly preferably from 100 to 100 000, in particular from 100 to 20 000, preferably physically separate mixing chambers connected in parallel.

In the process of the invention, mixing of the starting materials is effected in a plurality of physically separate chambers connected in parallel and the streams are preferably recombined at a later point, preferably for further work-up. This arrangement which preferably has a large number of parallel streams and at first glance appears complicated has the advantage that even relatively high reaction temperatures can be controlled and set very well as a result of the relatively large surface area of the reactor. Owing to the relatively high temperatures which can in this way be employed industrially, undesirable by-products such as amine hydrochlorides, ureas, carbamyl chlorides can be suppressed or avoided. In addition, the relatively high temperatures which are possible enable shorter residence times and thus a reduction in the reactor volume with a corresponding lower phosgene hold-up to be achieved.

The higher reaction temperature which is possible according to the invention compared to the known phosgenation in the liquid phase allows the known disadvantages of liquid-phase phosgenation, namely, in particular, solids formation and long after reaction times, to be avoided.

The residence time in the reaction zone is thus also reduced in the process of the invention. A lower residence time leads to better product quality and, due to the size of the apparatus, permits a lower phosgene and solvent hold-up compared to the prior art.

In the process of the invention, the mixing chambers are primarily the points at which the amine is brought into contact with the phosgene. However, the mixing chambers are preferably not merely pure mixing devices but are part of the reaction space or represent the reaction space in which the phosgenation primarily takes place. For the present purposes, the expression reaction space preferably refers to the space in which the reaction mixture has the preferred reaction temperature. The parallel streams of the various mixing chambers can be combined to form a single stream within the reaction space. As an alternative, it is also possible to cool the reaction mixture before the streams are combined and combine and work-up the streams only subsequently.

According to the invention, phosgene and amine are thus brought into contact in a plurality of mixing chambers. The phosgene and the amine are preferably fed through separate inlets into each of the mixing chambers. This means that each mixing chamber has at least one inlet for phosgene and at least one inlet for the amine. The individual inlets for each mixing chamber can be supplied by a single feed line for phosgene or amine. This means that a supply line for phosgene and one for the amine are split up into individual feed lines for the individual mixing chambers whose streams are combined again at a later point and worked up together. Thus, a phosgene stream and an amine stream can each preferably be split up into a plurality of individual streams and the individual streams can be fed to the mixing chambers, with each mixing chamber having at least one phosgene inlet and at least one amine inlet.

The volume of the individual mixing chambers is from 0.01 cm$^3$ and 1 l, preferably from 0.01 to 10 cm$^3$, particularly preferably from 0.01 to 1 cm$^3$. For the present purposes, the volume of the mixing chamber is the volume which the individual mixing chamber has between the point at which the amine comes together with the phosgene and the point at which this stream comes together with the stream from a further mixing chamber connected in parallel. Here, the volume of the space in which the amine comes together with the phosgene is included.

As indicated at the outset, the parallel arrangement of a plurality of mixing chambers has the advantage that, compared to a plant of the same capacity having a single stream, the individual parallel streams are smaller and can thus be controlled better in terms of temperature. Microstructured mixing chambers are preferably used as mixing chambers. Microstructured mixing chambers are generally known and have been described many times. A general presentation on microstructured mixing chambers may be found in Chemical Micro Process Engineering, V. Hessel et al., 2004, 200-214.

These microstructured mixing chambers offer to a particular degree the advantage that particularly good and reliable temperature control can be achieved as a result of the large surface area to volume ratio of the mixing chamber or the reaction space.

Laminar diffusion mixers, multilamination mixers, micromixers having structured walls, split-recombine mixers, free-jet mixers and/or nozzles are preferably used as mixing chambers; particular preference is given to using T- or Y-mixers.

In laminar diffusion mixers, the mixing of substreams of the fluid, which has been divided up on a microstructure into many microscopically small flow lamellae having a thickness in the range from 10 to 2000 μm or from 20 to 1000 μm or from 40 to 500 μm, occurs exclusively by molecular diffusion perpendicular to the main flow direction. An approximate design of the mixer can be achieved via the Fourier number $Fo=T/T_D$. If the residence time T is at least in the order of magnitude of the diffusion time $T_D$ for transverse mixing, i.e. the Fourier number has a value of at least 1, virtually complete molecular mixing is achieved at the outlet of the mixer.

Laminar diffusion mixers can be configured as simple T- or Y-mixers or as multilamination mixers. In T- or Y-mixers, the two substreams to be mixed are fed via a T- or Y-shaped arrangement into a single channel. The channel width $\delta_c$ is critical to the transverse diffusion displacement $S_{diff}$. At a typical channel width of from 100 μm to 1 mm, very short mixing times of less than 100 ms are obtained for gases, while the mixing times in the case of liquids are in the range of minutes. If liquids or supercritical fluids are mixed, as in the case of the present process, it is advantageous for the mixing process to be additionally aided, for example by means of flow-induced transverse mixing.

In multilamination mixers, the substreams to be mixed are geometrically divided into a plurality of flow threads in a divider and then alternately fed into lamellae of the mixing section at the outlet of the divider. In the case of liquids, mixing times in the range of seconds are achieved using classical multilamination mixers. Since this is not sufficient for some applications (e.g. in the case of fast reactions), the basic principle has been developed further so that the flow lamellae are additionally focused geometrically or hydrodynamically. In the case of geometric focusing, this is achieved by a constriction in the mixing section, and in the case of hydrodynamic focusing it is achieved by means of two side streams which flow perpendicularly onto the main stream and thus compress the flow lamellae further. The focusing described allows lateral dimensions of the flow lamellae of a few microns to be realized, so that even liquids can be mixed within a few 10 s of microseconds.

In the case of micromixers having structured walls, secondary structures, for example grooves or fins, are arranged on the channel walls at a particular angle to the main flow direction, preferably 45° or 90°.

Split-recombine mixers have stages of recurring separation and combination of streams. In each of these stages, the number of lamellae is successively doubled and thickness of the lamellae and diffusion displacement are thereby halved.

In the case of nozzles, mixing of the starting materials occurs in a mixing zone without moving internals by utilizing the turbulence which is present or is produced. To avoid by-products, mixing should occur in a time of less than 1 s, preferably less than 0.1 s. The two feed streams phosgene and amine, the latter diluted with an inert solvent is appropriate, are fed separately into the mixing zone. The feed streams can enter the mixing zone via in each case one or more entry cross sections of any shape. Preference is given to circular, elliptical, annular and rectangular cross sections. The main flow direction in the mixing zone can be at any angle in the range from 0° (parallel introduction) to 180° (countercurrent arrangement) to the main flow directions of the introduced feed streams in the entry cross section. The inflowing feed streams can be accelerated before entry into the mixing zone. The mixing zone can be a space having any geometric shape. It is preferably a rotationally symmetric or mirror-symmetric volume which is bounded by solid walls with the exception of the inflow and outflow cross sections. In one embodiment (coaxial nozzle), the amine stream is fed in via a circular cross section, while the phosgene is fed in via an annulus. The arrangement of the entry cross sections is coaxial with the axis of the cylindrical mixing zone. The normal to the entry cross section of the amine forms an angle of 0° with the axis of the cylinder. The normal to the entry cross section of the phosgene stream forms an angle of from 0 to 90° with the axis of the cylinder. In a further alternative embodiment (annular nozzle), the amine stream, if appropriate diluted with an inert solvent, is fed in via an annular gap. This is coaxial with the likewise annular or circular mixing zone. The phosgene stream is fed in via two annular gaps which are likewise arranged coaxially to the axis of the mixing zone and enclose the annular gap for the introduction of amine. In a further alternative embodiment, the amine stream is fed centrally and coaxially into a rotationally symmetric mixing zone. The phosgene stream is fed in via one or more cross sections which are distributed around the outer circumference of the mixing zone and whose normals form an angle of from 60 to 90° with the axis of the mixing zone.

The mixing chambers can be made of materials which are generally known for this purpose and are resistant to corrosion by the reaction mixture, e.g. Hasteloy (HC4, HB2), titanium, tantalum, glass, ceramic. The mixing chambers can particularly preferably be based on Hasteloy and/or glass.

The mixing zone adjoins a reaction space in which reaction of the mixed components occurs. The reaction space can have any geometric shape. Preference is given to rotationally symmetric and mirror-symmetric volumes. The cross section of the reaction space (perpendicular to the main flow direction) can remain constant, widen or narrow over the length.

As indicated at the outset, the expression "mixing chamber" comprises the parallel streams between the contacting of amine and phosgene to the combining with one of the parallel mixing chambers. Thus, after mixing of the phosgene with the amine in the mixing chambers, the streams from the individual mixing chambers are preferably brought together and preferably worked up together.

The reaction of the amine with the phosgene is preferably carried out at a temperature of greater than 180° C., preferably in the range from 220° C. to 300° C., in particular from 230° C. to 270° C. The reaction temperature is thus preferably close to or higher than the temperature at which dissociation of the hydrochlorides of the amines employed commences. This preferred reaction temperature also defines the expression "reaction space" in this text as the space in which the reaction mixture has this temperature. The heating/cooling of the reaction mixture can be effected, for example, by heat being introduced or removed by means of structures, e.g. channels, which are close to (e.g. opposite) the reaction zone and through which a heat transfer medium is passed. Heat is particularly preferably removed via thermal conduction by the material of the reaction apparatus; in this way, for example, the heat can be conducted by thermal conduction from the reaction space to the entry region for the starting materials and be transferred to these. For this purpose, the starting materials preferably have the appropriate entry temperature. In the case of highly exothermic reactions, the removal of heat can be supported by generally known measures.

The amine is preferably introduced into the mixing chambers at a temperature of greater than 180° C., preferably greater than 230° C., particularly preferably in the range from 230° C. to 300° C., in particular from 230° C. to 270° C. The amine can particularly preferably be introduced into the mixing chambers in admixture with an inert organic solvent which is generally known for this purpose, preferably benzene, toluene, xylene, dichlorobenzene, monochlorobenzene, preferably in a proportion by weight of from 5 to 90% by weight, based on the total weight of amine and solvent.

Amine and phosgene are preferably fed into the mixing chambers in a molar ratio of amine to phosgene in the range from 1:2 to 1:20, particularly preferably from 1:4 to 1:13, i.e. the reaction is carried out at an appropriate excess of phosgene over the amine.

The phosgene can preferably be introduced into the mixing chambers at a temperature of greater than 180° C., particularly preferably in the range from 220° C. to 300° C., in particular from 240° C. to 270° C.

As a result of the combination of high temperature with a high phosgene concentration in the reaction mixture, the duration of the preparation of isocyanate is greatly shortened and the formation of by-products (e.g. amine hydrochlorides and substituted ureas) is suppressed and the yields of secondary by-products are reduced. This makes it possible to prepare various monoisocyanates, diisocyanates and polyisocyanates from amines and phosgene in high yield in a single temperature stage and in a single pass through the reactor.

The reaction of the amine with the phosgene is preferably carried out at a pressure in the range from 20 to 100 bar, particularly preferably from 30 bar to 60 bar. The pressure is thus preferably selected as a function of the properties of the solvent used and is preferably equal to or higher than the pressure required to keep all constituents of the reaction mixture in the liquid phase.

In a preferred embodiment, the time for which the starting materials remain in the hot reaction zone generally does not exceed 5-60 seconds, with the time depending on the nature of the amine. The residence time of the reaction mixture at a temperature of greater than 180° C., preferably in the range from 220° C. to 300° C., in particular from 230° C. to 270° C., is particularly preferably less than 60 s, preferably in the range from 0.01 to 30 s, particularly preferably from 0.1 s to 2 s. The residence time can be determined as indicated in DE-A 17 68 439.

After the reaction, the reaction mixture is preferably cooled rapidly, e.g. by depressurization of the reaction stream, in order to avoid formation of secondary and subsequent components. In one possible embodiment, this cooling can be effected by rapid removal of reactive components, e.g. HCl. As a result of the decrease in pressure, low-boiling components firstly evaporate and cool the mixture as a result of the heat of vaporization and the mixture is then cooled further by expansion of the gas volume. In other embodiments, cooling can be effected by mixing in cooler streams (quench) or by withdrawing heat via the boundary walls. A combination of the embodiments mentioned is also possible. Thus, the reaction mixture is preferably cooled to a temperature in the range from 180 to 40° C.; the reaction mixture is particularly preferably cooled after a residence time of less than 60 s, preferably in the range from 0.01 to 30 s, particularly preferably from 0.1 s to 2 s, at a temperature of greater than 180° C., preferably in the range from 220° C. to 300° C., in particular from 230° C. to 270° C., to a temperature in the range from 180° C. to 40° C. The reaction mixture is particularly preferably cooled after a residence time of less than 60 s, preferably in the range from 0.05 to 30 s, particularly preferably from 0.1 s to 2 s, at a temperature of greater than 180° C., preferably in the range from 220° C. to 300° C., in particular from 230° C. to 270° C., by at least 50° C. in less than 1 s by depressurizing the reaction mixture by at least 20 bar.

Due to the separate mixing chambers and reaction spaces, the process of the invention offers the advantage over known processes that the reaction temperature can be controlled very well. This makes it possible to control the reaction safely even at very high reaction mixtures and avoid overheating and thus decompression and formation of undesirable by-products. The temperature of the reaction mixture preferably changes by less than 20° C. during the residence time of less than 60 s, preferably in the range from 0.05 to 30 s, particularly preferably from 0.1 s to 2 s, at a temperature of preferably greater than 180° C., more preferably in the range from 220° C. to 300° C., in particular from 230° C. to 270° C., i.e. the temperature of the reaction mixture is kept largely constant within the reaction space.

To prepare the isocyanates, it is possible to use generally known amines which are customary for this purpose. The amines can be used individually or in admixture with other amines in the customary grades and purities. Possible amines are, in particular, known primary amines, diamines or polyamines. Preference is given to using 2,2'-, 2,4'- and/or 4,4'-diaminodiphenylmethane (MDA), 2,4- and/or 2,6-toluenediamine (TDA), 1-amino-3,3,5-trimethyl-5-aminomethylcyclohexane (isophoronediamine, IPDA) and/or hexamethylenediamine (HDA), particularly preferably 2,2'-, 2,4'- and/or 4,4'-diaminodiphenylmethane (MDA) and/or 2,4- and/or 2,6-toluenediamine (TDA) as amine.

As indicated at the outset, the phosgenation preferably takes place in the liquid phase, i.e. the amine is preferably present in the liquid phase during the phosgenation.

The isocyanate prepared by the phosgenation can be purified by conventional methods, for example distillation. Phosgene and if appropriate solvent can preferably be largely removed, particularly preferably completely removed, from the reaction mixture of the phosgenation in a first purification step. This purification step can preferably be carried out by means of a stripping process. In such a stripping process, the isocyanate can be introduced into an apparatus having a large internal surface area and be distributed over its surface so that volatile components can be given off. The apparatus can be, by way of example and preferably, a falling film evaporator or thin film evaporator or a packed column of appropriate design. Inert gases can be fed in as stripping medium and/or reduced pressure can be applied to the apparatus. The temperatures during this stripping process are preferably below 200° C., particularly preferably from 50 to 190° C. The desired isocyanate can preferably be distilled off under known conditions, preferably at pressures of from 2 to 50 mbar and temperatures of from 150 to 250° C.

The purification of the isocyanate is particularly preferably carried out by removing phosgene, HCl and if appropriate solvent from the isocyanate at a temperature of <150° C., preferably from 50 to 149° C., for example in a stripping process as described above, if appropriate under reduced pressure or with introduction of inert gas, and, preferably after complete removal of the phosgene at a temperature of ≦190° C., preferably from 150 to 190° C., separating off solvent from the isocyanate, for example in a stripping process as described above, with the purification steps being able to be carried out using the above-described apparatuses, and subsequently separating off the isocyanate by distillation at pressures of from 2 to 50 mbar, preferably from 2 to 20 mbar, and temperatures of from 150 to 250° C., preferably from 180 to 230° C.

These purification processes offer the advantage that chlorine-comprising compounds which lead to adverse properties in the desired isocyanate are removed from the isocyanate.

The unreacted excess phosgene and the solvent are, after separation from the reaction products, preferably recirculated into the materials circuit.

EXAMPLES

Preparation of MDI 180 ml/h of a 22.8% strength MDA solution in MCB and 195 ml/h of liquid phosgene were passed through a split and recombine micromixer at a temperature of 245° C. and 55 bar in a molar ratio of MDA/phosgene of 1/12. The starting materials were each passed through 600 mm long $1/16$" tubes and preheated before mixing. After mixing in this 0.02 ml reactor, the reaction stream was continuously depressurized and introduced into a separator. In the separator, the product was stripped free of phosgene and HCl by means of nitrogen. The product was subsequently distilled at 70 mbar and 50-60° C. to free it of solvent.

Preparation of TDI 210 ml/h of a 17.2% strength TDA solution in MCB and 195 ml/h of liquid phosgene were passed through a T-shaped laminar diffusion mixture having a volume of 0.27 ml at a temperature of 245° C. and 55 bar in a molar ratio of TDA/phosgene of 1/7. The starting materials were each passed through 600 mm long $1/16$" tubes and preheated before mixing. After mixing in this reactor, the reaction stream was continuously depressurized and introduced into a separator. In the separator, the product was stripped free of phosgene and HCl by means of nitrogen. The product was subsequently distilled at 70 mbar and 50-60° C. to free it of solvent.

According to the invention, a large number of the reactors presented in these examples can be connected in parallel, with the streams from the various reactors after mixing of the amine with the phosgene being combined and worked up jointly.

The invention claimed is:

1. A process for preparing isocyanates by phosgenation of amines, comprising:
   mixing phosgene and an amine together in at least 2 mixing chambers connected in parallel, with the mixing chambers being part of the reaction space or representing the reaction space, wherein the volume of each individual mixing chamber is in the range from 0.01 cm$^3$ to 1 liter, and
   conducting the reaction of the amine with the phosgene at a temperature of greater than 180° C. and at a pressure in the range from 20 to 100 bar, the residence time of the reaction mixture at a temperature of greater than 180° C. being less than 60 s,
   wherein the reaction of the amine with the phosgene is conducted in mixing chambers or reaction spaces all of which are connected in parallel.

2. The process according to claim 1, wherein the phosgene and the amine are fed through separate inlets into each of the mixing chambers.

3. The process according to claim 1, wherein microstructured mixing chambers are employed as mixing chambers.

4. The process according to claim 1, wherein said mixing chambers are selected from the group consisting of laminar diffusion mixers, multilamination mixers, micromixers having structured walls, split-recombine mixers, free-jet mixers and nozzles.

5. The process according to claim 3, wherein the mixing chambers are formed of Hasteloy and/or glass.

6. The process according to claim 1, wherein a phosgene stream and an amine stream are each split into a plurality of individual streams and the individual streams are fed into the mixing chambers, with each mixing chamber having at least one phosgene inlet and at least one amine inlet.

7. The process according to claim 1, wherein, after mixing of the phosgene with the amine in the mixing chambers, the streams from the individual mixing chambers are brought together.

8. The process according to claim 1, wherein the amine is introduced into the mixing chambers at a temperature of greater than 180° C.

9. The process according to claim 1, wherein the amine is introduced into the mixing chambers as a mixture with an inert organic solvent in an amount of 5 to 90% by weight, based on the total weight of amine and solvent.

10. The process according to claim 1, wherein amine and phosgene are fed into the mixing chambers in a molar ratio of amine to phosgene in the range from 1:2 to 1:20.

11. The process according to claim 1, wherein the phosgene is introduced into the mixing chambers at a temperature of greater than 180° C.

12. The process according to claim 1, wherein the reaction mixture is cooled after a residence time of less than 60 s at a temperature of greater than 180° C. to a temperature in the range from 40° C. to 180° C.

13. The process according to claim 1, wherein the reaction mixture is cooled after a residence time of less than 60 s at a temperature of greater than 180° C. by at least 50° C. in less than 1 s by depressurizing the reaction mixture by at least 20 bar.

14. The process according to claim 12, wherein the temperature of the reaction mixture changes by less than 20° C. during the residence time of less than 60 s.

15. The process according to claim 1, wherein said amine reactant is selected from the group consisting of 2,2'-, 2,4'- and/or 4,4'-diamino-diphenylmethane (MDA), 2,4- and/or 2,6-toluenediamine (TDA), 1-amino-3,3,5-trimethyl-5-aminomethylcyclohexane (isophoronediamine, IPDA) and/or hexamethylenediamine (HDA).

16. The process according to claim 1, wherein the amine is present in the liquid phase during the phosgenation reaction.

17. The process according to claim 1, wherein a solvent is mixed with said phosgene and amine reactants.

18. The process according to claim 17, wherein the isocyanate reaction product is purified by removing phosgene, HCl and solvent from the isocyanate at a temperature of <150° C. and, after removal of the phosgene, at a temperature of $\leqq$190° C., separating solvent from the isocyanate, and subsequently
   separating the isocyanate by distillation at pressures ranging from 2 to 50 mbar and temperatures ranging from 150 to 250° C.

19. The process according to claim 1, wherein the reaction of the amine with the phosgene is conducted to form the isocyanates in a single stage reaction.

20. The process according to claim 1, wherein the reaction of the amine with the phosgene is conducted in a single stream in the reaction space.

21. The process according to claim 1, wherein the reaction of the amine with the phosgene is conducted in mixing chambers or reaction spaces each having the same volume.

22. The process according to claim 1, wherein the reaction of the amine with the phosgene is conducted under pressure until the reaction is complete.

23. The process according to claim 1, wherein during the contacting the amine and the phosgene from the parallel mixing chambers are brought together.

* * * * *

UNITED STATES PATENT AND TRADEMARK OFFICE
CERTIFICATE OF CORRECTION

PATENT NO. : 8,212,069 B2  
APPLICATION NO. : 12/446460  
DATED : July 3, 2012  
INVENTOR(S) : Ralf Boehling et al.

It is certified that error appears in the above-identified patent and that said Letters Patent is hereby corrected as shown below:

On the title page, Items (73) and (74), information has been omitted. Items (73) and (74) should read:

-- (73) Assignee: BASF SE, Ludwigshafen (DE)

(74) Attorney, Agent, or Firm - Oblon, Spivak, McClelland, Maier & Neustadt, L.L.P. --

Signed and Sealed this
Twenty-fifth Day of September, 2012

David J. Kappos
*Director of the United States Patent and Trademark Office*